United States Patent [19]
Marz et al.

[11] Patent Number: 5,670,511
[45] Date of Patent: Sep. 23, 1997

[54] INDOLEPIPERIDINE DERIVATIVES

[75] Inventors: Joachim Marz, Mainz; Hartmut Greiner, Weiterstadt; Christoph Seyfried, Seeheim; Gerd Bartoszyk, Weiterstadt, all of Germany

[73] Assignee: Merck Patent Gesellschaft Mit Beschrankter Haftung, Darmstadt, Germany

[21] Appl. No.: 586,273

[22] Filed: Jan. 16, 1996

[30] Foreign Application Priority Data

Jan. 12, 1995 [DE] Germany ............... 19500689.5

[51] Int. Cl.[6] ............... C07D 513/04; A61K 31/395
[52] U.S. Cl. ............... 514/290; 514/309; 514/307; 514/311; 514/312; 514/319; 514/320; 514/326; 546/99; 546/101; 546/148; 546/169; 546/176; 546/177; 546/201
[58] Field of Search ............... 546/99, 101, 148, 546/169, 176, 177, 201; 514/290, 309, 307, 311, 312, 319, 320, 326

[56] References Cited

U.S. PATENT DOCUMENTS

| | | | |
|---|---|---|---|
| 4,530,932 | 7/1985 | Clemence et al. ............... | 514/318 |

FOREIGN PATENT DOCUMENTS

| | | | |
|---|---|---|---|
| 112191 | 6/1984 | European Pat. Off. ...... | C07D 401/04 |
| 184 258 | 6/1986 | European Pat. Off. ...... | C07D 401/06 |
| 303 506 | 2/1989 | European Pat. Off. ...... | C07D 401/04 |
| 324 431 | 7/1989 | European Pat. Off. ...... | C07D 401/04 |
| 2621588 | 4/1989 | France ............... | C07D 409/14 |
| 2675801 | 10/1992 | France ............... | C07D 417/14 |
| 2184443 | 12/1986 | United Kingdom ......... | C07D 401/14 |
| 2198729 | 12/1987 | United Kingdom ......... | C07D 401/14 |
| 92/00070 | 1/1992 | WIPO ............... | C07D 401/04 |

OTHER PUBLICATIONS

Malleron et al., "New Indole Derivatives as Potent and Selective Serotonin Uptake Inhibitors", J. Med. Chem. 36, pp. 1194–1202, 1993.

*Primary Examiner*—Robert T. Bond
*Attorney, Agent, or Firm*—Millen, White, Zelano & Branigan, P.C.

[57] ABSTRACT

Indolepiperidine derivatives of the formula I

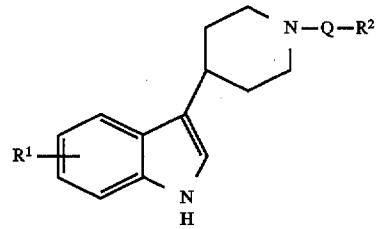

and their physiologically acceptable salts exhibit action on the central nervous system, in particular dopamine-agonistic or dopamine-antagonistic action.

17 Claims, No Drawings

INDOLEPIPERIDINE DERIVATIVES

SUMMARY OF THE INVENTION

The invention relates to indolepiperidine derivatives of the formula I

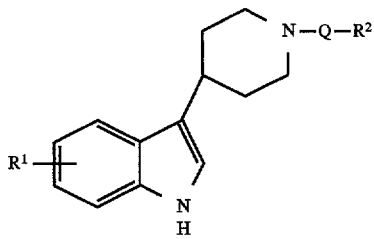

in which $R^1$ is H, A, OH, OA, F, CL, Br, I, $CF_3$, $OCF_3$, CN, COOH, $CONH_2$, CONHA, $CONA_2$ or COOA, $R^2$ is —NH—CO—Ar, —NH—$SO_2$—Ar or D, Q is $C_mH_{2m}$ or O—$C_nH_{2n}$ D is

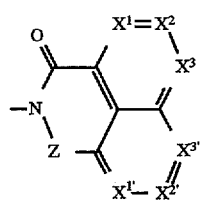

$X^1$, $X^2$ and $X^3$ and also $X^{1'}$, $X^{2'}$ and $X^{3'}$ are in each case independently of one another N or CH, where the respective H atoms can also be replaced by a substituent selected from the group consisting of A, OA, F, Cl, Br, I, $CF_3$, $OCF_3$, CN, COOH and COOA, Z is CO, $SO_2$ or SO, A is alkyl having 1 to 6 C atoms, Ar is 1-naphthyl which is unsubstituted or mono- or disubstituted by A, OA, F, Cl, Br, I, CF3, $OCF_3$, CN, COOH or COOA, where one, two, three or four CH groups can likewise be replaced by N, m is 1, 2, 3 or 4 and n is 1, 2 or 3, and their physiologically acceptable salts.

An object of the invention is finding novel compounds which can be used for the production of medicaments.

Upon further study of the specification and appended claims, further objects and advantages of this invention will become apparent to those skilled in the art.

It has been found that the compounds of the formula I and their physiological acceptable acid addition salts have useful pharmacological properties. Thus they show, in particular, actions on the central nervous system, especially serotonin-agonistic and -antagonistic actions. They inhibit serotonin reabsorption and the binding of tritiated serotonin ligands to hippocampal receptors (Cossery et al., European J. Pharmacol. 140 (1987), 143–155). In particular, they bind to $5HT_2$ and $D_2$ receptors. Changes in DOPA accumulation in the striatum and 5-HTP accumulation in N. raphe additionally occur (Seyfried et at., European J. Pharmacol. 160 (1989), 31–41). Analgesic and hypotensive actions furthermore occur; thus in conscious, spontaneously hypertensive rats (strain SHR/Okamoto/NIH-MO-CHB-Kissleg; method cf. Weeks and Jones, Proc. SOC. Exptl. Biol. Med. 104 (1960), 646–648) carrying catheters, the directly measured blood pressure is decreased after oral administration of the compounds. They are also suitable as prophylaxis and for the control of the sequelae of cerebral infarct (Apoplexia cerebri), such as stroke and cerebral ischeamias, and also for the treatment of extra-pyrimidal motor side-effects of neuroleptics and of Parkinson's disease. The compounds are also suitable for the prophylaxis and for the treatment of obsessive compulsive disorders, anxiety states, panic attacks, depressions, psychoses, schizophrenia, delusional obsessions, Alzheimer's disease, migraine, anorexia, bulimia and drug abuse.

Compounds of the formula I and their physiologically acceptable acid addition salts can therefore be used, for example, as pharmaceutical active substances for anxiolytics, antidepressants and/or antihypertensives and also as intermediates for the preparation of other pharmaceutical active compounds.

The invention relates to the indole derivatives of the formula I and to their physiologically acceptable acid addition salts.

The radical A is alkyl having 1, 2, 3, 4, 5 or 6, in particular 1 or 2, C atoms, preferably methyl, furthermore also ethyl, n-propyl, isopropyl, n-butyl, isobutyl, sec-butyl or tert-butyl. OA is preferably methoxy, furthermore also ethoxy, n-propoxy, isopropoxy, n-butoxy, isobutoxy, sec -butoxy or tert-butoxy. NHA is preferably methylamino, further ethylamino, n-propylamino, isopropylamino, n-butylamino, isobutylamino, sec-butylamino or tert-butylamino. $NA_2$ is preferably dimethylamino, furthermore N-ethyl-N-methylamino, diethylamino, di-n-propylamino, diisopropylamino or di-n-butylamino.

Resulting from this, CO—NHA is particularly preferably N-methylcarbamoyl or N-ethylcarbamoyl and CO—$NA_2$ is preferably N,N-dimethylcarbamoyl or N,N-diethylcarbamoyl.

The indole radicals which are bonded to the piperidine radical in the 3-position are otherwise unsubstituted or monosubstituted. The substituents $R^1$, is preferably located in the 5- or 6-position, but furthermore also in the 4- or 7-positions.

Preferred substituents $R^1$ on the indolyl radical are, for example, $CO_2H$, $CO_2CH_3$, $OCH_3$, OH, F, CN or $CONH_2$.

Q is preferably $C_mH_{2m}$, where the parameter m is preferably 2 or 3.

$R^2$ is preferably 1- or 2-carboxamidonaphthyl, 2-, 3-, 4-, 5-, 6-, 7- or 8-carboxamidoquinolinyl, 1-, 3-, 4-, 5-, 6-, 7- or 8-carboxamidoisoquinolinyl, 1- or 2-sulfonamidonaphthyl, 2-, 3-, 4-, 5-, 6-, 7- or 8-sulfonamidoquinolinyl, 1-, 3-, 4-, 5-, 6-, 7- or 8-sulfonamidoisoquinolinyl, 2,3-dihydro-1H-benz [de]isoquinoline-1,3-dione radical or a 2,3-dihydro-1H-benz [de]isoquinolin-1-one radical. The radicals mentioned can also be substituted. Preferred substituents are OA, CN, F, Cl or Br.

The invention accordingly relates in particular to those compounds of the formula I in which at least one of the radicals mentioned has one of the preferred meanings indicated above. Some preferred groups of compounds can also be expressed by the formulae Ia to If below, which correspond to the formula I and in which the radicals which are not described in greater detail have the meaning indicated in the formula I, but in which in Ia $R^1$ is F, Cl, Br or I and $R^2$ is carboxamidonaphthyl or sulfonamidonaphthyl;

in Ib $R^1$ is F, Cl, Br or I and $R^2$ is carboxamidoquinolinyl or sulfonamidoquinolinyl;

in Ic $R^1$ is F, Cl, Br or I and $R^2$ is a 2,3-dihydro-1H-benz[de]isoquinoline-1,3-dione radical;

Id $R^1$ is F, and $R^2$ is carboxamidonaphthyl or sulfonamidonaphthyl and $R^1$ is located in the 4-position of the indole radical;

in Ie $R^1$ is F, $R^2$ is carboxamidoquinolinyl or sulfonamidoquinolinyl and $R^1$ is located in the 5- or 6-position of the indole radical;

in If $R^1$ is F and $R^2$ is a 2,3-dihydro-1H-benz[de]isoquinoline-1,3-dione radical and $R^1$ is located in the 5- or 6-position of the indole radical.

In particular, however, preferred are those compounds of the subformulae Ig and Iag to Ifg which correspond to the formula I and the subformulae Ia to If, but in which Q is additionally —$CH_2$—$CH_2$—, —$CH_2$—$CH_2$—$CH_2$— or —O—$CH_2$—$CH_2$—.

The invention furthermore relates to a process for the preparation of indolepiperidine derivatives of the formula I according to claim 1, and of their salts, characterized in that a compound of the formula II

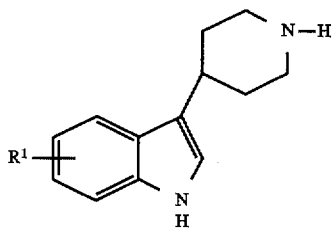

II in which $R^1$ has the meaning indicated, is reacted with a compound of the formula III

  III in which

L, if Q is

—$C_mH_{2m}$, is Cl, Br, I, OH, O—CO—A', O—CO—Ph, O—$SO_2$—A', O—$SO_2$—Ph or another reactive esterified OH group or easily nucleophilically substitutable leaving group and L, if Q is —O—$C_nH_{2n}$— is H, —CO—A', —CO—Ph, —$SO_2$—A' or —$SO_2$—Ph, or another reactive esterified OH group or easily nucleophilically substitutable leaving group and where, in both cases, Ph is phenyl or tolyl and A' is alkyl or fluoroalkyl, $R^2$ and Q have the meanings indicated, or in that a compound of the formula IV

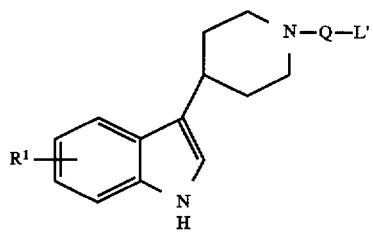

IV in which

L' is Cl, Br, I, OH, O—CO—A', O—CO—Ph, O—$SO_2$—A', O—$SO_2$—Ph, where Ph is phenyl or tolyl and A' is alkyl or fluoroalkyl, or another reactive esterified OH group or easily nucleophilically substitutable leaving group and $R^1$ and Q have the meanings indicated, is reacted with a primary or secondary amino compound of the formula V

 V in which $R^2$ has the meaning indicated, or in that a compound of the formula VI

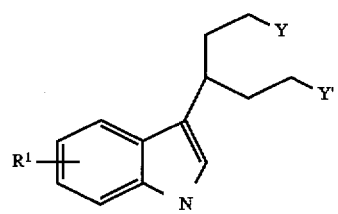

VI in which

Y and Y' can be identical or different and are Cl, Br, I, OH, O—CO—A', O—CO—Ph, O—$SO_2$—A', O—$SO_2$—Ph, where Ph is phenyl or tolyl and A' is alkyl or fluoroalkyl, or another reactive esterified OH group or easily nucleophilically substitutable leaving group and $R^1$ has the meaning indicated, is reacted with an amine of the formula VII

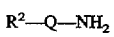 VII in which $R^2$ and Q have the meanings indicated, or in that a compound otherwise corresponding to the formula I, but which instead of one or more hydrogen atoms contains one or more reducible groups and/or one or more additional C—C and/or C—N bonds, is treated with a reducing agent, or in that a compound otherwise corresponding to the formula I, but which instead of one or more hydrogen atoms contains one or more solvolyzable groups, is treated with a solvolyzing agent, and/or in that a radical $R^1$ is optionally converted into another radical $R^1$ by cleaving, for example, an OA group with the formation of an OH group and/or a CN, COOH or COOA group is converted into another functional group, and/or in that a base or acid of the formula I obtained is converted into one of its salts by treating with an acid or base.

The compounds of the formula I are otherwise prepared by methods known per se, such as are described in the literature (e.g. in standard works such as Houben-Weyl, Methoden der Organischen Chemie (Methods of Organic Chemistry), Georg-Thieme Verlag, Stuttgart; Organic Reactions, John Wiley & Sons, Inc. New York; J. March, Adv. Org. Chem., 3rd Ed. J. Wiley & Sons (1985), namely under reaction conditions which are known and suitable for the reactions mentioned. Use can also be made in this case of variants which are known per se but not mentioned here in greater detail.

If desired, the starting substances for the claimed process can also be formed in situ in such a way that they are not isolated from the reaction mixture but immediately reacted further to give the compounds of the formula I.

A preferred method for the preparation of compounds of the formula I consists in reacting a 3-(4-piperidyl)indole derivative of the formula II with an electrophilic compound of the formula III.

The compounds of the formulae II and, in particular, III are known in some cases; the unknown compounds of the formula II and III can easily be prepared analogously to the known compounds.

3-(4-Piperidyl)indoles of the formula II can be prepared, for example, by reaction of 4-halopiperidines, where halogen is preferably chlorine or bromine, with indole or corresponding derivatives substituted by $R^1$. These reactions are known per se and are carried out under customary reaction conditions as are known from the literature for the electrophilic substitution of indoles.

Compounds of the formula III can be prepared, for example, by reacting a compound of the formula Ar—$CONH_2$, Ar—$SO_2NH_2$ or D—H, where Ar and D have the meanings indicated, with a compound of the formula L—Q—L' under the customary conditions of N-alkylation.

Primary alcohols of the formula III are obtainable, for example, by reduction of the corresponding carboxylic acids or their esters. Treating with thionyl chloride, hydrogen bromide, phosphorus tribromide or similar halogen compounds yields the corresponding halides of the formula III (Hal: Br, Cl). The corresponding sulfonyloxy compounds are obtainable from the alcohols by reaction with the corresponding sulfonyl chlorides.

The reaction of the compounds II and III proceeds according to methods which are known from the literature for the alkylation of amines. The components can be reacted with one another without the presence of a solvent, optionally in a closed tube or in an autoclave. However, it is preferable to react the compounds in the presence of an inert solvent. Suitable solvents are, for example, hydrocarbons, such as benzene, toluene, xylene; ketones such as acetone, butanone; alcohols such as methanol, ethanol, isopropanol, n-butanol; ethers such as tetrahydrofuran (THF) or dioxane; amides such as dimethylformamide (DMF) or N-methylpyrrolidone; nitriles such as acetonitrile, and, if appropriate, also mixtures of these solvents with one another or mixtures with water.

The reaction time, depending on the conditions used, is preferably from a few minutes to about 14 days, the reaction temperature is preferably from approximately 0° to 150° C., particularly from 20° to 130° C.

In some cases, the addition of an acid-binding agent, for example of an alkali or alkaline earth metal hydroxide, carbonate or bicarbonate or of another salt of a weak acid of the alkali metals or alkaline earth metals, preferably of potassium, sodium or calcium, or the addition of an organic base such as triethylamine, dimethylaniline, pyridine or quinoline can favor the reaction. In other cases, the addition of catalytic amounts of an acid, preferably of a mineral acid, such as HCl, is favorable.

It is further possible to obtain a compound of the formula I by reacting a compound of the formula V with an indole derivative of the formula IV.

The indoles of the formula IV can be prepared by the various possibilities of indole synthesis known per se, for example the Fischer indole synthesis. It is additionally particularly preferred to react, for example, appropriately substituted 4-halopiperidines with indoles substituted by $R^1$ to give compounds of the formula IV.

Compounds of the formula V are generally known and can be prepared, for example, by conversion of the corresponding carboxylic acids Ar—COOH or sulfonic acids Ar—$SO_2OH$ to the respective amides.

The reaction of the compounds IV and V proceeds according to methods such as are known from the literature for the reactions of amines or amides with electrophilic reaction components. The components can be reacted with one another directly without the presence of a solvent, if appropriate in a closed tube or in an autoclave, under normal pressure or at elevated pressure, an inert gas such as, for example, $N_2$ being added to increase the pressure. However, it is also possible to react the compounds in the presence of an inert solvent. Suitable solvents are those previously mentioned for the reaction of II with III.

The optimum reaction time, depending on the reaction conditions selected, is preferably from a few minutes to about 14 days, and the reaction temperature preferably from approximately 0° C. to 150° C. usually between 20° C. and 130° C.

It is furthermore possible to react an indole derivative of the formula VI with an amine of the formula VII in order to obtain a compound of the formula I.

Indoles of the formula VI can be obtained, for example, via an electrophilic substitution in the 3-position of an indole by reaction with a compound of the formula Y—$(CH_2)_2$—CH(Hal)—$(CH_2)_2$—Y', in which Hal is, for example, Cl or Br, while the compounds of the formula VII can be obtained by alkylation of the corresponding amides, sulfonamides or amines of the formula $R^2$—H with a compound of the formula L—Q—$NH_2$, the $NH_2$ group expediently being blocked by amino protective groups known per se.

The reaction of the compounds VI with the amines VII proceeds according to methods such as are known from the literature for the alkylation of amines and have previously been briefly described for the reaction of compound II with compound III.

It is furthermore possible to obtain a compound of the formula I by treating a preliminary product which, instead of hydrogen atoms, contains one or more reducible groups and/or one or more additional C—C and/or C—N bonds, with a reducing agent, preferably at temperatures from about −80° to +250° C. in the presence of at least one inert solvent.

Groups which are reducible (replaceable by hydrogen) are, in particular, oxygen in a carbonyl group, hydroxyl, arylsulfonyloxy (e.g. p-toluenesulfonyloxy), N-benzenesulfonyl, N-benzyl or O-benzyl.

It is fundamentally possible to convert compounds which only contain one or those which contain two or more of the abovementioned groups or additional bonds next to one another, reductively to a compound of the formula I. In this case, substituents in the indole radicals which are contained in the starting compound can be reduced at the same time. Nascent hydrogen or complex metal hydrides, furthermore Wolff-Kishner reduction and reductions with hydrogen gas under transition metal catalysis are preferably also used for this purpose.

Compounds which otherwise correspond to the formula I, but instead of one or more H atoms contain one or more solvolyzable groups, can furthermore be solvolyzed, in particular hydrolyzed, to give the compounds of the formula I.

Thus 1-acylindole derivatives (corresponding to the formula I, but containing an acyl group, preferably an alkanoyl, alkylsulfonyl or arylsulfonyl group in each case having up to 10 C atoms, such as methane-, benzene- or p-toluenesulfonyl, in the 1-position of the indole radical) can in particular be hydrolyzed to the corresponding indole derivatives which are unsubstituted in the 1-position of the indole ring, e.g. in acidic or, better, in neutral or alkaline medium at temperatures from about 0° to 200° C. Bases used are expediently sodium hydroxide, potassium hydroxide, calcium hydroxide, sodium carbonate, potassium carbonate or ammonia. The solvent selected is preferably water; lower alcohols such as methanol, ethanol; ethers such as THF, dioxane; sulfones such as tetramethylene sulfone; or mixtures thereof, particularly the water-containing mixtures. Hydrolysis can also be carried out by treating with water, in particular at boiling heat.

A compound of the formula I can furthermore be converted to another compound of the formula I by methods known per se.

Compounds of the formula I in which the indole system is substituted, for example, by COOA, $CONH_2$, CONHA or $CONA_2$ can be obtained by derivatization of corresponding carboxyindol-3-yl compounds. For example, the acids or their reactive derivatives, such as their acid halides or anhydrides, can be esterified with appropriate alcohols or alkoxides, using the methods known per se or one of the numerous variants. It is furthermore possible to amidate acids, acid halides or esters with primary or secondary aliphatic or cyclic amines. The reaction of the free carboxylic acid with the amine under the conditions of a peptide synthesis is preferred. This reaction preferably proceeds in the presence of a dehydrating agent, e.g. a carbodiimide such as dicyclohexylcarbodiimide or N-(3-dimethylaminopropyl)-N-ethylcarbodiimide, furthermore propane-phosphonic anhydride (cf. Angew. Chemie 92, 129 (1980)), diphenylphosphoryl azide or 2-ethoxy-N-ethoxycarbonyl-1,2-dihydroquinoline, in an inert solvent, e.g. a halogenated hydrocarbon such as dichloromethane, an ether such as THF or dioxane, an amide such as DMF or dimethylacetamide, or a nitrile such as acetonitrile, at temperatures from approximately $-10°$ to $40°$ C., preferably from $0°$ to $30°$ C. Instead of the acid or the amide, reactive derivatives of these substances can also be employed in the reaction, e.g. those in which reactive groups are intermediately blocked by protective groups. The acids can also be used in the form of their activated esters, which are expediently formed in situ, e.g. by addition of 1-hydroxybenzotriazole or N-hydroxysuccinimide.

Cyano-substituted indol-3-yl radicals can furthermore be hydrolyzed to carboxyindol-3-yl or carbamidoindol-3-yl radicals.

Compounds of the formula I in which the indole radicals are mono- or disubstituted by O-alkyl can be subjected to an ether cleavage, the corresponding hydroxy derivatives being formed. For example, the ether groups can be cleaved by treating with dimethyl sulfide-boron tribromide complex, e.g. in toluene, ethers such as THF or dimethyl sulfoxide, or by fusing with pyridine or aniline hydrohalides, preferably pyridine hydrochloride, at approximately $150°-250°$ C.

A base of the formula I obtained can be converted into the associated acid addition salt using an acid. Acids which yield physiologically acceptable salts are suitable for this reaction. Thus inorganic acids can be used, e.g. sulfuric acid, hydrohalic acids such as hydrochloric acid or hydrobromic acid, phosphoric acids such as orthophosphoric acid, nitric acid, sulfamic acid, furthermore organic acids, specifically aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfuric acid.

If desired, the free bases of the formula I can be liberated from their salts by treatment with strong bases such as sodium hydroxide or potassium hydroxide, or sodium carbonate or potassium carbonate, if no other acidic groups are present in the molecule. In those cases where the compounds of the formula I have free acid groups, salt formation can likewise be achieved by treatment with bases. Suitable bases are alkali metal hydroxides, alkaline earth metal hydroxides or organic bases in the form of primary, secondary or tertiary amines.

The invention furthermore relates to the use of the compounds of the formula I and their physiologically acceptable salts for the production of pharmaceutical preparations, in particular by non-chemical routes. In this connection, they can be brought into a suitable dosage form together with at least one excipient or auxiliary and optionally in combination with one or more other active compounds.

The invention furthermore relates to compositions, in particular pharmaceutical preparations, comprising at least one compound of the formula I and/or one of its physiologically acceptable salts. These preparations can be employed as medicaments in human and veterinary medicine. Possible excipients are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc or petroleum jelly. Tablets, coated tablets, capsules, syrups, juices, drops or suppositories are in particular used for enteral administration, solutions, preferably oily or aqueous solutions, furthermore suspensions, emulsions or implants for parenteral administration, and ointments, creams or powders for topical application. The novel compounds can also be lyophilized and the lyophilizates obtained used, for example, for the production of injection preparations.

The preparations indicated can be sterilized and/or comprise auxiliaries such as lubricants, preservatives, stabilizers and/or wetting agents, emulsifiers, salts for affecting the osmotic pressure, buffer substances, colorants, flavorings and/or aromatic substances. If desired, they can also comprise one or more further active compounds, e.g. one or more vitamins.

The compounds of the formula I and their physiologically acceptable salts can be used in the therapeutic treatment of the human or animal body and in the control of diseases. They are suitable for the treatment of extrapyramidal motor side-effects of neuroleptics, of disorders of the central nervous system such as states of tension, depressions and/or psychoses and of side-effects in the treatment of hypertension (e.g. with α-methyldopa). The compounds can furthermore be used in endocrinology and gynaecology, e.g. for the therapy of acromegaly, hypogonadism, secondary amenorrhoea, premenstrual syndrome, undesired puerperal lactation, furthermore for the prophylaxis and therapy of cerebral disorders (e.g. migraine), in particular in geriatrics, similarly to certain ergot alkaloids and for the control of the sequelae of cerebral infarct (Apoplexia cerebri), such as stroke and cerebral ischemias.

The substances according to the invention are generally administered in this case in analogy to known, commercially available preparations, e.g. bromocryptine and dihydroergocornine, preferably in doses from approximately 0.2 to 500 mg, in particular from about 0.2 to 50 mg, per dose unit. The daily dose is preferably from approximately 0.001 to 10 mg/kg of body weight. The low doses (approximately 0.2 to 1 mg per dose unit; approximately 0.001 to 0.005 mg/kg of body weight) are in this case in particular suitable for use as anti-migraine agents; for the other indications doses of from 10 to 50 mg per dose unit are preferred. The specific dose for each intended patient depends, however, on all sorts of factors, for example on the activity of the specific compound employed, on the age, body weight, general state of health, sex, on the diet, on the time and route of administration, and on the excretion rate, pharmaceutical substance combination and severity of the particular disorder to which the therapy applies. Oral administration is preferred.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. DE 195 00 689.5, filed Jan. 12, 1995 is hereby incorporated by reference.

In the examples below, "customary working up" means: Water is added if necessary, the mixture is extracted with dichloromethane, the organic phase is separated off, dried over sodium sulfate, filtered and evaporated, and the residue is purified by chromatography on silica gel and/or by crystallization. Temperatures are indicated in °C. In the cases in which the substances tend to decompose, the $R_f$ values are indicated as an alternative.

EXAMPLES

Example 1

1.2 g of 2-(2-chloroethyl)-2,3-dihydro-1H-benz[de]isoquinoline-1,3-dione ("A") [obtainable by reaction of 2,3-dihydro-1H-benz[de]isoquinoline-1,3-dione with 1,2-dichloroethane to give 2-(2-chloroethyl)- 2,3-dihydro-1H-benz[de]isoquinoline-1,3-dione] and 1.0 g of 4-(5-fluoroindol-3-yl)piperidine [obtainable by reaction of N-BOC-4-chloropiperidine with 5-fluoroindole and subsequent removal of the protective group] are dissolved in 200 ml of acetonitrile and the mixture is stirred at room temperature for 8 hours. Customary working up gives 2-[2-(4-(5-fluoro-3-indolyl)piperidino)ethyl]-2,3-dihydro-1H-benz[de]isoquinoline-1,3-dione, tetrahydrate, m.p. 235°.

The following are obtained analogously by reaction of "A"

with 4-(4-fluoroindol-3-yl)piperidine: 2-[2-(4-(4-fluoro-3-indolyl)piperidino)ethyl]-2,3-dihydro-1H-benz[de]isoquinoline-1,3-dione, $R_f$=0.82 (ethyl acetate/methanol 3:1);

with 4-(6-fluoroindol-3-yl)piperidine: 2-[2-(4-(6-fluoro-3-indolyl)piperidino)ethyl]-2,3-dihydro-1H-benz[de]isoquinoline-1,3-dione, m.p. 264° with 4-(5-methoxyindol-3-yl)piperidine: 2-[2-(4-(5-methoxy-3-indolyl)piperidino)ethyl]-2,3-dihydro-1H-benz[de]isoquinoline-1,3-dione;

with 4-(6-methoxyindol-3-yl)piperidine: 2-[2-(4-(6-methoxy-3-indolyl)piperidino)ethyl]-2,3-dihydro-1H-benz[de]isoquinoline-1,3-dione;

with 4-(5-trifluoromethoxyindol-3-yl)piperidine: 2-[2-(4-(5-trifluoromethoxy-3-indolyl)piperidino)ethyl]-2,3-dihydro-1H -benz[de]isoquinoline-1,3-dione;

with 4-(4-cyanoindol-3-yl)piperidine: 2-[2-(4-(4-cyano-3-indolyl)piperidino)ethyl]-2,3-dihydro-1H-benz[de]isoquinoline-1,3-dione;

with 4-(6-cyanoindol-3-yl)piperidine: 2-[2-(4-(6-cyano-3-indolyl)piperidino)ethyl]-2,3-dihydro-1H-benz[de]isoquinoline-1,3-dione;

with 4-(5-cyanoindol-3-yl)piperidine: 2-[2-(4-(5-cyano-3-indolyl)piperidino)ethyl]-2,3-dihydro-1H -benz[de]isoquinoline-1,3-dione;

with 4-(6-trifluoromethylindol-3-yl)piperidine: 2-[2-(4-(6-trifluoromethyl-3-indolyl)piperidino)ethyl]-2,3-dihydro-1H-benz[de]isoquinoline-1,3-dione;

with 4-(4-trifluoromethylindol-3-yl)piperidine: 2-[2-(4-(4-trifluoromethyl-3-indolyl)piperidino)ethyl-2,3-dihydro-1H-benz[de]isoquinoline-1,3-dione;

with 4-(5-methoxycarbonylindol-3-yl)piperidine: 2-[2-(4-(5-methoxycarbonyl-3-indolyl)piperidino)ethyl]-2,3-dihydro-1H-benz[de]isoquinoline-1,3-dione;

with 4-(6-methoxycarbonylindol-3-yl)piperidine: 2-[2-(4-(6-methoxycarbonyl-3-indolyl)piperidino)ethyl]-2,3-dihydro-1H-benz[de]isoquinoline-1,3-dione;

with 4-(4-methoxycarbonylindol-3-yl)piperidine: 2-[2-(4-(4-methoxycarbonyl-3-indolyl)piperidino)ethyl-2,3-dihydro-benz[de]isoquinoline-1,3-dione;

with 4-(5-chloroindol-3-yl)piperidine: 2-[2-(4-(5-chloro-3-indolyl)piperidino)ethyl]-2,3-dihydro-1H-benz[de]isoquinoline-1,3-dione;

with 4-(6-chloroindol-3-yl)piperidine: 2-[2-(4-(6-chloro-3-indolyl)piperidino)ethyl]-2,3-dihydro-1H-benz[de]isoquinoline-1,3-dione;

with 4-(4-chloroindol-3-yl)piperidine: 2-[2-(4-(4-chloro-3-indolyl)piperidino)ethyl]-2,3-dihydro-1H-benz[de]isoquinoline-1,3-dione.

Example 2

0.8 g of 2-[2-(4-(5-methoxycarbonyl-3-indolyl)piperidino)ethyl]-2,3-dihydro-1H-benz[de]isoquinoline-1,3-dione[obtainable according to Example 1] is heated with 100 ml of 2N ethanolic KOH for 0.5 hours and worked up in the customary manner, and 2-[2-(4-(5-carboxy-3-indolyl)piperidino)ethyl]-2,3-dihydro-1H-benz[de]isoquinoline-1,3-dione is obtained.

The following are obtained analogously by hydrolysis of the corresponding esters starting from 2-[2-(4-(6-methoxycarbonyl-3-indolyl)piperidino)ethyl]-2,3-dihydro-1H-benz[de]isoquinoline-1,3-dione:

2-[2-(4-(6-carboxy-3-indolyl)piperidino)ethyl]-2,3-dihydro-1H-benz[de]isoquinoline-1,3-dione;

from 2-[2-(4-(4-methoxycarbonyl-3-indolyl)piperidino)ethyl]-2,3-dihydro-1H-benz[de]isoquinoline-1,3-dione:

2-[2-(4-(4-carboxy-3-indolyl)piperidino)ethyl]-2,3-dihydro-1H-benz[de]isoquinoline-1,3-dione.

Example 3

Analogously to Example 1, starting from 1-(2-aminoethyl)-4-(5-fluoroindol-3-yl)piperidine [obtainable by reaction of N-BOC-4-chloropiperidine with 5-fluoroindole, subsequent removal of the protective group and reaction with 1-chloro-2-aminoethane] and 8-quinolinesulfonyl chloride ("B"), customary working up gives N-[2-(4-(5-fluoro-3-indolyl)piperidino)ethyl]-8-quinolinesulfonamide, hydrochloride hemihydrate, m.p. 290°.

The following are obtained analogously by reaction of "B"

with 1-(2-aminoethyl)-4-(4-fluoroindol-3-yl)piperidine: N-[2-(4-(4-fluoro-3-indolyl)piperidino)ethyl]-8-quinolinesulfonamide;

with 1-(2-aminoethyl)-4-(6-fluoroindol-3-yl)piperidine: N-[2-(4-(6-fluoro-3-indolyl)piperidino)ethyl]-8-quinolinesulfonamide, hydrochloride, m.p. 276°;

with 4-(5-ethoxyindol-3-yl)piperidine: N-[2-(4-(5-ethoxy-3-indolyl)piperidino)ethyl]-8-quinolinesulfonamide;

with 4-(5-methoxyindol-3-yl)piperidine: N-[2-(4-(5-methoxy-3-indolyl)piperidino)ethyl]-8-quinolinesulfonamide;

with 4-(6-methoxyindol-3-yl)piperidine: N-[2-(4-(6-methoxy-3-indolyl)piperidino)ethyl]-8-quinolinesulfonamide;

with 4-(5-trifluoromethoxyindol-3-yl)piperidine: N-[2-(4-(5-trifluoromethoxy-3-indolyl)piperidino)ethyl]-8-quinolinesulfonamide;

with 4-(4-cyanoindol-3-yl)piperidine: N-[2-(4-(4-cyano-3-indolyl)piperidino)ethyl]-8-quinolinesulfonamide;

with 4-(6-cyanoindol-3-yl)piperidine: N-[2-(4-(6-cyano-3-indolyl)piperidino)ethyl]-8-quinolinesulfonamide;

with 4-(5-cyanoindol-3-yl)piperidine: N-[2-(4-(5-cyano-3-indolyl)piperidino)ethyl]-8-quinolinesulfonamide;

with 4-(6-trifluoromethylindol-3-yl)piperidine: N-[2-(4-(6-trifluoromethyl-3-indolyl)piperidino)ethyl]-8-quinolinesulfonamide;

with 4-(4-trifluoromethylindol-3-yl)piperidine: N-[2-(4-(4-trifluoromethyl-3-indolyl)piperidino)ethyl]-8-quinolinesulfonamide;

with 4-(5-methoxycarbonylindol-3-yl)piperidine: N-[2-(4-(5-methoxycarbonyl-3-indolyl)piperidino)ethyl]-8-quinolinesulfonamide;

with 4-(6-methoxycarbonylindol-3-yl)piperidine: N-[2-(4-(6-methoxycarbonyl-3-indolyl)piperidino)ethyl]-8-quinolinesulfonamide;

with 4-(4-methoxycarbonylindol-3-yl)piperidine: N-[2-(4-(4-methoxycarbonyl-3-indolyl)piperidino)ethyl]-8-quinolinesulfonamide;

with 4-(5-chloroindol-3-yl)piperidine: N-[2-(4-(5-chloro-3-indolyl)piperidino)ethyl]-8-quinolinesulfonamide;

with 4-(6-chloroindol-3-yl)piperidine: N-[2-(4-(6-chloro-3-indolyl)piperidino)ethyl]-8-quinolinesulfonamide;

with 4-(4-chloroindol-3-yl)piperidine: N-[2-(4-(4-chloro-3-indolyl)piperidino)ethyl]-8-quinolinesulfonamide.

Example 4

Analogously to Example 2, hydrolysis of N-[2-(4-(5-methoxycarbonyl-3-indolyl)piperidino)ethyl]-8-quinolinesulfonamide gives N-[2-(4-(5-carboxy-3-indolyl)piperidino)ethyl]-8-quinolinesulfonamide.

The following are obtained analogously by hydrolysis of the corresponding esters starting from N-[2-(4-(6-methoxycarbonyl-3-indolyl)piperidino)-ethyl]-8-quinolinesulfonamide: N-[2-(4-(6-carboxy-3-indolyl)piperidino)ethyl]-8-quinolinesulfonamide;

from N-[2-(4-(4-methoxycarbonyl-3-indolyl)piperidino)-ethyl]-8-quinolinesulfonamide: N-[2-(4-(4-carboxy-3-indolyl)piperidino)ethyl]-8-quinolinesulfonamide.

Example 5

2.1 g of 2-[2-(4-(5-carboxy-3-indolyl)piperidino)ethyl]-2,3-dihydro-1H-benz[de]isoquinoline-1,3-dione are suspended in 100 ml of N-methylpyrrolidine. 3.2 g of 2-chloro-1-methylpyridinium methanesulfonate are then added and the mixture is stirred at room temperature for 12 hours. Dried NH$_3$ gas is passed into the resulting solution until it is saturated and the mixture is stirred again for 10 hours. Customary working up gives 2-[2-(4-(5-carbamoyl-3-indolyl)piperidino)ethyl]-2,3-dihydro-1H-benz[de]isoquinoline-1,3-dione.

The following are obtained analogously by amidation of the following carboxylic acids:

from 2-[2-(4-(6-carboxy-3-indolyl)piperidino)ethyl]-2,3-dihydro-1H-benz[de]isoquinoline-1,3-dione: 2-[2-(4-(6-carbamoyl-3-indolyl)piperidino)ethyl]-2,3-dihydro-1H-benz[de]isoquinoline-1,3-dione;

from 2-[2-(4-(4-carboxy-3-indolyl)piperidino)ethyl]-2,3-dihydro-1H-benz[de]isoquinoline-1,3-dione: 2-[2-(4-(4-carbamoyl-3-indolyl)piperidino)ethyl]-2,3-dihydro-1H-benz[de]isoquinoline-1,3-dione;

from N-[2-(4-(5-carboxy-3-indolyl)piperidino)ethyl]-8-quinolinesulfonamide: N-[2-(4-(5-carbamoyl-3-indolyl)piperidino)ethyl]-8-quinolinesulfonamide;

from N-[2-(4-(6-carboxy-3-indolyl)piperidino)ethyl]-8-quinolinesulfonamide: N-[2-(4-(6-carbamoyl-3-indolyl)piperidino)ethyl]-8-quinolinesulfonamide;

from N-[2-(4-(4-carboxy-3-indolyl)piperidino)ethyl]-8-quinolinesulfonamide: N-[2-(4-(4-carbamoyl-3-indolyl)piperidine)ethyl]-8-quinolinesulfonamide.

Example 6

A solution of 3.9 g of 2-[2-(4-(5-carboxy-3-indolyl)piperidino)ethyl]-2,3-dihydro-1H-benz[de]isoquinoline-1,3-dione in 250 ml of DMF is treated with 1 g of N-methylmorpholine. A solution of two equivalents of tert-butylamine in 5 ml of DMF, 1.3 g of 1-hydroxybenzotriazole and a solution of 1.9 g of N-(3-dimethylaminopropyl)-N'-ethylcarbodiimide hydrochloride in 20 ml of DMF is added with stirring. The mixture is stirred at room temperature for 16 hours and the filtrate is evaporated. Customary working up gives 2-[2-(4-(5-N-tert-butylcarbamoyl-3-indolyl)piperidino)ethyl]-2,3-dihydro-1H-benz[de]isoquinoline-1,3-dione.

The following are obtained analogously by reaction with tert-butylamine starting from 2-[2-(4-(6-carboxy-3-indolyl)piperidino)ethyl]-2,3-dihydro-1H-benz[de]isoquinoline-1,3-dione: 2-[2-(4-(6-N-tert-butylcarbamoyl-3-indolyl)piperidino)ethyl]-2,3-dihydro-1H-benz[de]isoquinoline-1,3-dione;

from 2-[2-(4-(4-carboxy-3-indolyl)piperidino)ethyl]-2,3-dihydro-1H-benz[de]isoquinoline-1,3-dione: 2-[2-(4-(4-N-tert-butylcarbamoyl-3-indolyl)piperidino)ethyl]-2,3-dihydro-1H-benz[de]isoquinoline-1,3-dione;

from N-[2-(4-(5-carboxy-3-indolyl)piperidino)-ethyl]-8-quinolinesulfonamide: N-[2-(4-(5-N-tert-butylcarbamoyl-3-indolyl)piperidino)ethyl]-8-quinolinesulfonamide;

from N-[2-(4-(6-carboxy-3-indolyl)piperidino)ethyl]-8-quinolinesulfonamide: N-[2-(4-(6-N-tert-butylcarbamoyl-3-indolyl)piperidino)ethyl]-8-quinolinesulfonamide;

from N-[2-(4-(4-carboxy-3-indolyl)piperidino)ethyl]-8-quinolinesulfonamide: N-[2-(4-(4-N-tert-butylcarbamoyl-3-indolyl)piperidino)ethyl]-8-quinolinesulfonamide.

Example 7

A mixture of 1.6 g of 2-[2-(4-(5-methoxy-3-indolyl)piperidino)ethyl]-2,3-dihydro-1H-benz[de]isoquinoline-1, 3-dione [which can be prepared according to Example 1], 1.8 g of pyridine hydrochloride and 50 ml of pyridine is boiled for 3 hours. The mixture is cooled, evaporated, worked up in the customary manner and gives 2-[2-(4-(5-hydroxy-3-indolyl)piperidino)ethyl]-2,3-dihydro-1H-benz[de]isoquinoline-1,3-dione.

The following are obtained analogously from 2-[2-(4-(6-methoxy-3-indolyl)piperidino)ethyl]-2,3-dihydro-1H-benz[de]isoquinoline-1,3-dione: 2-[2-(4-(5-hydroxy-3-indolyl)piperidino)ethyl]-2,3-dihydro-1H-benz[de]isoquinoline-1,3-dione;

from N-[2-(4-(5-methoxy-3-indolyl)piperidino)ethyl]-8-quinolinesulfonamide: N-[2-(4-(5-hydroxy-3-indolyl)piperidino)ethyl]-8-quinolinesulfonamide;

from N-[2-(4-(6-methoxy-3-indolyl)piperidino)-ethyl]-8-quinolinesulfonamide: N-[2-(4-(6-hydroxy-3-indolyl)piperidino)ethyl]-8-quinolinesulfonamide.

Example 8

Analogously to Example 1, reaction of 1-(3-aminopropyl)-4-(6-fluoro-3-indolyl)piperidine [obtainable by reaction of 6-fluoroindole with N-BOC-4-chloropiperidine, subsequent removal of the protective group and reaction with 1-chloro-3-aminopropane] with 1-isoquinolinecarbonyl chloride ("C") in 200 ml of acetonitrile gives, after customary working up, N-[3-(4-(6-fluoro-3-indolyl)piperidino)-propyl]-1-isoquinolinecarboxamide, dihydrochloride tetrahydrate, $R_f$=0.33 (ethyl acetate/methanol 4:1; 1% triethylamine).

The following are obtained analogously by reaction of "C"

- with 1-(3-aminopropyl)-4-(4-fluoroindol-3-yl)piperidine: N-[3-(4-(4-fluoro-3-indolyl)piperidino)propyl]-1-isoquinolinecarboxamide;
- with 1-(3-aminopropyl)-4-(6-fluoroindol-3-yl)piperidine: N-[3-(4-(6-fluoro-3-indolyl)piperidino)propyl]-1-isoquinolinecarboxamide;
- with 1-(3-aminopropyl)-4-(5-methoxyindol-3-yl)piperidine: N-[3-(4-(5-methoxy-3-indolyl)piperidino)propyl]-1-isoquinolinecarboxamide;
- with 1-(3-aminopropyl)-4-(6-methoxyindol-3-yl)piperidine: N-[3-(4-(6-methoxy-3-indolyl)piperidino)propyl]-1-isoquinolinecarboxamide;
- with 1-(3-aminopropyl)-4-(5-trifluoromethoxyindol-3-yl)piperidine: N-[3-(4-(5-trifluoromethoxy-3-indolyl)piperidino)propyl]-1-isoquinolinecarboxamide;
- with 1-(3-aminopropyl)-4-(4-cyanoindol-3-yl)piperidine: N-[3-(4-(4-cyano-3-indolyl)piperidino)propyl]-1-isoquinolinecarboxamide;
- with 1-(3-aminopropyl)-4-(6-cyanoindol-3-yl)piperidine: N-[3-(4-(6-cyano-3-indolyl)piperidino)propyl]-1-isoquinolinecarboxamide;
- with 1-(3-aminopropyl)-4-(5-cyanoindol-3-yl)piperidine: N-[3-(4-(5-cyano-3-indolyl)piperidino)propyl]-1-isoquinolinecarboxamide;
- with 1-(3-aminopropyl)-4-(6-trifluoromethylindol-3-yl)piperidine: N-[3-(4-(6-trifluoromethyl)-3-indolyl)piperidino)propyl]-1-isoquinolinecarboxamide;
- with 1-(3-aminopropyl)-4-(4-trifluoromethylindol-3-yl)piperidine: N-[3-(4-(4-trifluoromethyl-3-indolyl)piperidino)propyl]-1-isoquinolinecarboxamide;
- with 1-(3- aminopropyl)-4-(5-methoxycarbonylindol-3-yl)piperidine: N-[3-(4-(5-methoxycarbonyl-3-indolyl)piperidino)propyl]-1-isoquinolinecarboxamide;
- with 1-(3- aminopropyl)-4-(6-methoxycarbonylindol-3-yl)piperidine: N-[3-(4-(6-methoxycarbonyl-3-indolyl)piperidino)propyl]-1-isoquinolinecarboxamide;
- with 1-(3-aminopropyl)-4-(4-methoxycarbonylindol-3-yl)piperidine: N-[3-(4-(4-methoxycarbonyl-3-indolyl)piperidino)propyl]-1-isoquinolinecarboxamide;
- with 1-(3-aminopropyl)-4-(5-chloroindol-3-yl)piperidine: N-[3-(4-(5-chloro-3-indolyl)piperidino)propyl]-1-isoquinolinecarboxamide;
- with 1-(3-aminopropyl)-4-(6-chloroindol-3-yl)piperidine: N-[3-(4-(6-chloro-3-indolyl)piperidino)propyl]-1-isoquinolinecarboxamide;
- with 1-(3-aminopropyl)-4-(4-chloroindol-3-yl)piperidine: N-[3-(4-(4-chloro-3-indolyl)piperidino)propyl]-1-isoquinolinecarboxamide.

Example 9

Analogously to Example 1, reaction of 1-(3-aminopropyl)-4-(6-fluoro-3-indolyl)piperidine [obtainable by reaction of 6-fluoroindole with N-BOC-4-chloropiperidine, subsequent removal of the protective group and reaction with 1-chloro-3-aminopropane] with 6-methoxyquinoline-4-carbonyl chloride in 200 ml of acetonitrile gives, after customary working up, N-[3-(4-(6-fluoro-3-indolyl)-piperidino)propyl]-6-methoxyquinoline-4-carboxamide, dihydrochloride hydrate, $R_f$=0.33 (ethyl acetate/methanol 4:1; 1% triethylamine).

The following are obtained analogously by reaction of 4-quinolinecarbonyl chloride

- with 1-(3-aminopropyl)-4-(4-fluoroindol-3-yl)piperidine: N-[3-(4-(4-fluoro-3-indolyl)piperidino)propyl]-4-quinolinecarboxamide;
- with 1-(3-aminopropyl)-4-(6-fluoroindol-3-yl)piperidine: N-[3-(4-(6-fluoro-3-indolyl)piperidino)propyl]-4-quinolinecarboxamide;
- with 1-(3-aminopropyl)-4-(5-methoxyindol-3-yl)piperidine: N-[3-(4-(5-methoxy-3-indolyl)piperidino)propyl]-4-quinolinecarboxamide;
- with 1-(3-aminopropyl)-4-(6-methoxyindol-3-yl)piperidine: N-[3-(4-(6-methoxy-3-indolyl)piperidino)propyl]-4-quinolinecarboxamide;
- with 1-(3-aminopropyl)-4-(5-trifluoromethoxyindol-3-yl)piperidine: N-[3-(4-(5-trifluoromethoxy-3-indolyl)piperidino)propyl]-4-quinolinecarboxamide;
- with 1-(3-aminopropyl)-4-(4-cyanoindol-3-yl)piperidine: N-[3-(4-(4-cyano-3-indolyl)piperidino)propyl]-4-quinolinecarboxamide;
- with 1-(3-aminopropyl)-4-(6-cyanoindol-3-yl)piperidine: N-[3-(4-(6-cyano-3-indolyl)piperidino)propyl]-4-quinolinecarboxamide;
- with 1-(3-aminopropyl)-4-(5-cyanoindol-3-yl)piperidine: N-[3-(4-(5-cyano-3-indolyl)piperidino)propyl]-4-quinolinecarboxamide;
- with 1-(3-aminopropyl)-4-(6-trifluoromethylindol-3-yl)piperidine: N-[3-(4-(6-trifluoromethyl-3-indolyl)piperidino)propyl]-4-quinolinecarboxamide;
- with 1-(3-aminopropyl)-4-(4-trifluoromethylindol-3-yl)piperidine: N-[3-(4-(4-trifluoromethyl-3-indolyl)piperidino)propyl]-4-quinolinecarboxamide;
- with 1-(3-aminopropyl)-4-(5-methoxycarbonylindol-3-yl)piperidine: N-[3-(4-(5-methoxycarbonyl-3-indolyl)piperidino)propyl]-4-quinolinecarboxamide;
- with 1-(3-aminopropyl)-4-(6-methoxycarbonylindol-3-yl)piperidine: N-[3-(4-(6-methoxycarbonyl-3-indolyl)piperidino)propyl]-4-quinolinecarboxamide;

with 1-(3-aminopropyl)-4-(4-methoxycarbonylindol-3-yl)piperidine: N-[3-(4-(4-methoxycarbonyl-3-indolyl)piperidino)propyl]-4-quinolinecarboxamide;

with 1-(3-aminopropyl)-4-(5-chloroindol-3-yl)piperidine: N-[3-(4-(5-chloro-3-indolyl)piperidino)propyl]-4-quinolinecarboxamide;

with 1-(3-aminopropyl)-4-(6-chloroindol-3-yl)piperidine: N-[3-(4-(6-chloro-3-indolyl)piperidino)propyl]-4-quinolinecarboxamide;

with 1-(3-aminopropyl)-4-(4-chloroindol-3-yl)piperidine: N-[3-(4-(4-chloro-3-indolyl)piperidino)propyl]-4-quinolinecarboxamide.

The following are obtained analogously by reaction of 6-methoxyquinoline-4-carbonyl chloride.

with 1-(3-aminopropyl)-4-(4-fluoroindol-3-yl)piperidine: N-[3-(4-(4-fluoro-3-indolyl)piperidino)propyl]-6-methoxy-4-quinolinecarboxamide;

with 1-(3-aminopropyl)-4-(6-fluoroindol-3-yl)piperidine: N-[3-(4-(6-fluoro-3-indolyl)piperidino)propyl]-6-methoxy-4-quinolinecarboxamide;

with 1-(3-aminopropyl)-4-(5-methoxyindol-3-yl)piperidine: N-[3-(4-(5-methoxy-3-indolyl)piperidino)propyl]-6-methoxy-4-quinolinecarboxamide;

with 1-(3-aminopropyl)-4-(6-methoxyindol-3-yl)piperidine: N-[3-(4-(6-methoxy-3-indolyl)piperidino)propyl]-6-methoxy-4-quinolinecarboxamide;

with 1-(3-aminopropyl)-4-(5-trifluoromethoxyindol-3-yl)piperidine: N-[3-(4-(5-trifluoromethoxy-3-indolyl)piperidino)propyl]-6-methoxy-4-quinolinecarboxamide;

with 1-(3-aminopropyl)-4-(4-cyanoindol-3-yl)piperidine: N-[3-(4-(4-cyano-3-indolyl)piperidino)propyl]-6-methoxy-4-quinolinecarboxamide;

with 1-(3-aminopropyl)-4-(6-cyanoindol-3-yl)piperidine: N-[3-(4-(6-cyano-3-indolyl)piperidino)propyl]-6-methoxy-4-quinolinecarboxamide;

with 1-(3-aminopropyl)-4-(5-cyanoindol-3-yl)piperidine: N-[3-(4-(5-cyano-3-indolyl)piperidino)propyl]-6-methoxy-4-quinolinecarboxamide;

with 1-(3-aminopropyl)-4-(6-trifluoromethylindol-3-yl)piperidine: N-[3-(4-(6-trifluoromethyl-3-indolyl)piperidino)propyl]-6-methoxy-4-quinolinecarboxamide;

with 1-(3-aminopropyl)-4-(4-trifluoromethylindol-3-yl)piperidine: N-[3-(4-(4-trifluoromethyl-3-indolyl)piperidino)propyl]-6-methoxy-4-quinolinecarboxamide;

with 1-(3-aminopropyl)-4-(5-methoxycarbonylindol-3-yl)piperidine: N-[3-(4-(5-methoxycarbonyl-3-indolyl)piperidino)propyl]-6-methoxy-4-quinolinecarboxamide;

with 1-(3-aminopropyl)-4-(6-methoxycarbonylindol-3-yl)piperidine: N-[3-(4-(6-methoxycarbonyl-3-indolyl)piperidino)propyl]-6-methoxy-4-quinolinecarboxamide;

with 1-(3-aminopropyl)-4-(4-methoxycarbonylindol-3-yl)piperidine: N-[3-(4-(4-methoxycarbonyl-3-indolyl)piperidino)propyl]-6-methoxy-4-quinolinecarboxamide;

with 1-(3-aminopropyl)-4-(5-chloroindol-3-yl)piperidine: N-[3-(4-(5-chloro-3-indolyl)piperidino)propyl]-6-methoxy-4-quinolinecarboxamide;

with 1-(3-aminopropyl)-4-(6-chloroindol-3-yl)piperidine: N-[3-(4-(6-chloro-3-indolyl)piperidino)propyl]-6-methoxy-4-quinolinecarboxamide;

with 1-(3-aminopropyl)-4-(4-chloroindol-3-yl)piperidine: N-[3-(4-(4-chloro-3-indolyl)piperidino)propyl]-6-methoxy-4-quinolinecarboxamide.

Example 10

1.2 9 of 2-(2-chloroethoxy)-2,3-dihydro-1H-benz[de]isoquinoline-1,3-dione ("D") [obtainable by reaction of N-hydroxy-2,3-dihydro-1H-benz[de]isoquinoline-1,3-dione with 1,2-dichloroethane to give 2-(2-chloroethoxy)-2,3-dihydro-1H-benz[de]isoquinoline-1,3-dione] and 1.0 g of 4-(5-fluoroindol-3-yl)piperidine [obtainable by reaction of N-BOC-4-chloropiperidine with 5-fluoroindole and subsequent removal of the protective group] are dissolved in 200 ml of acetonitrile and the solution is stirred at room temperature for 8 hours. Customary working up gives 2-[2-(4-(5-fluoro-3-indolyl)piperidino)ethoxy]-2,3-dihydro-1H-benz[de]isoquinoline-1,3-dione, hydrochloride hydrate, m.p. 271°.

The following are obtained analogously by reaction of "D"

with 4-(4-fluoroindol-3-yl)piperidine: 2-[2-(4-(4-fluoro-3-indolyl)piperidino)ethoxy]-2,3-dihydro-1H-benz[de]isoquinoline-1,3-dione, hydrate, m.p. 162° (dec.);

with 4-(6-fluoroindol-3-yl)piperidine: 2-[2-(4-(6-fluoro-3-indolyl)piperidino)ethoxy]-2,3-dihydro-1H-benz[de]isoquinoline-1,3-dione, hydrochloride hydrate, m.p. 253°;

with 4-(7-ethylindol-3-yl)piperidine: 2-[2-(4-(7-ethyl-3-indolyl)piperidino)ethoxy]-2,3-dihydro-1H-benz[de]isoquinoline-1,3-dione, hydrochloride hemihydrate, m.p. 261°.

Example 11

Analogously to Example 1, starting from 1-(2-aminoethyl)-4-(6-fluoroindol-3-yl)piperidine ("E") [obtainable by reaction of N-BOC-4-chloropiperidine with 6-fluoroindole, subsequent removal of the protective group and reaction with 1-chloro-2-aminoethane] and 2-naphthalenecarbonyl chloride gives, after customary working up, N-[2-(4-(6-fluoro-3-indolyl)piperidino)ethyl]-2-naphthalenecarboxamide, hemihydrate, m.p. 194°.

The following are obtained analogously by reaction of "E"

with 1-naphthalenecarbonyl chloride N-[2-(4-(6-fluoro-3-indolyl)piperidino)ethyl]-1-naphthalenecarboxamide, hydrochloride sesquihydrate, m.p. 124°;

with 2-methyl-7-chloroquinoline-4-carbonyl chloride N-[2-(4-(6-fluoro-3-indolyl)piperidino)ethyl]-2-methyl-7-chloroquinoline-4-carboxamide, trihydrate, m.p. 206°.

with 4-methoxyquinoline-2-carbonyl chloride N-[2-(4-(6-fluoro-3-indolyl)piperidino)ethyl]-4-methoxyquinoline-2-carboxamide, dihydrochloride dihydrate, m.p. 198°;

with 3-quinolinecarbonyl chloride N-[2-(4-(6-fluoro-3-indolyl)piperidino)ethyl]-3-quinolinecarboxamide, hydrate, m.p. 176°;

with 2-quinolinecarbonyl chloride N-[2-(4-(6-fluoro-3-indolyl)piperidino)ethyl]-2-quinolinecarboxamide, dihydrochloride dihydrate, m.p. 132;

The following are obtained analogously by reaction of 1-(3-aminopropyl)-4-(6-fluoroindol-3-yl)piperidine with 2-naphthalenecarbonyl chloride N-[3-(4-(6-fluoro-3-indolyl)piperidino)propyl]-2-naphtalenecarboxamide, hydrochloride trihydrate, m.p. 102°;

with 1-naphthalenecarbonyl chloride N-[3-(4-(6-fluoro-3-indolyl)piperidino)propyl]-1-naphthalenecarboxamide, hydrochloride trihydrate, m.p. 85°;

with 2-methyl-7-chloroquinoline-4-carbonyl chloride N-[3-(4-(6-fluoro-3-indolyl)piperidino)propyl]-2-methyl-7-chloroquinoline-4-carboxamide, sesquihydrate, m.p. 89°;

with 4-methoxyquinoline-2-carbonyl chloride N-[3-(4-(6-fluoro-3-indolyl)piperidino)propyl]-4-methoxyquinoline-2-carboxamide, dihydrochloride dihydrate, m.p. 231°;

with 3-quinolinecarbonyl chloride N-[3-(4-(6-fluoro-3-indolyl)piperidino)propyl]-3-quinolinecarboxamide, dihydrochloride hemihydrate, m.p. 257°;

with 2-quinolinecarbonyl chloride N-[3-(4-(6-fluoro-3-indolyl)piperidino)propyl]-2-quinolinecarboxamide, dihydrochloride hydrate, m.p. 229.

The following examples relate to pharmaceutical preparations:

Example A

Injection Vials

A solution of 100 g of an active compound of the formula I and 5 g of disodium hydrogen phosphate are adjusted to pH 6.5 in 3 l of double-distilled water using 2N hydrochloric acid, sterile filtered, filled into injection vials, lyophilized under sterile conditions and aseptically sealed. Each injection vial contains 5 mg of active compound.

Example B

Suppositories

A mixture of 20 g of an active compound of the formula I is melted with 100 g of soya lecithin and 1400 g of cocoa butter, poured into moulds and allowed to cool. Each suppository contains 20 mg of active compound.

Example C

Solution

A solution is prepared from 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water. The solution is adjusted to pH 6.8, made up to 1 l and sterilized by irradiation. This solution can be used in the form of eye drops.

Example D

Ointments 500 mg of an active compound of the formula I are mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is pressed to give tablets in a customary manner such that each tablet comprises 10 mg of active compound.

Example F

Coated tablets

Tablets are pressed analogously to Example E and are then coated in a customary manner with a coating of sucrose, potato starch, talc, tragacanth and colourant.

Example G

Capsules 2 kg of active compound of the formula I are filled into hard gelatin capsules in a customary manner such that each capsule contains 20 mg of the active compound.

Example H

Ampoules

A solution of 1 kg of active compound of the formula I in 60 l of double-distilled water is sterile filtered, filled into ampoules, lyophilized under sterile conditions and aseptically sealed. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An indolepiperidine compound of the formula I

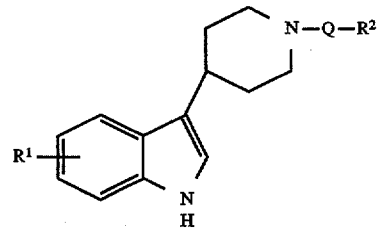

in which $R^1$ is H, A, OH, OA, F, Cl, Br, I, $CF_3$, $OCF_3$, CN, COOH, $CONH_2$, CONHA, $CONA_2$ or COOA, $R^2$ is —NH—CO—Ar, —NH—$SO_2$—Ar or D, Q is —$C_mH_{2m}$— or —O—$C_nH_{2n}$—

D is

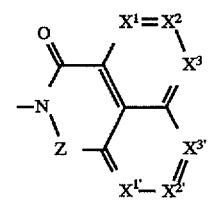

$X^1$, $X^2$ and $X^3$ and also $X^{1'}$, $X^{2'}$ and $X^{3'}$ are in each case independently of one another N or CH, where the respective H atoms can also be replaced by a substituent selected from the group consisting of A, OA, F, Cl, Br, I, $CF_3$, $OCF_3$, CN, COOH and COOA, Z is CO, $SO_2$ or SO, A is alkyl having 1 to 6 C atoms, Ar is 1-naphthyl which is unsubstituted or mono- or disubstituted by A, OA, F, Cl, Br, I, $CF_3$, CN, COOH or COOA, where one, two, three or four CH groups in the ring are optionally replaced by N m is 1, 2, 3 or 4 and n is 1, 2 or 3, and physiologically acceptable salts thereof.

2. The compound of claim 1, which is
 (a) 2-[2-(4-(5- Fluoro-3-indolyl)piperidino)ethyl-2,3-dihydro-1H-benz[de]isoquinoline-1,3-dione;
 (b) 2-[2-(4-(6-fluoro-3-indolyl)piperidino)ethyl]-2,3-dihydro-1H-benz[de]isoquinoline-1,3-dione;
 (c) 2-[2-(4-(4-fluoro-3-indolyl)piperidino)ethyl]-2,3-dihydro-1H-benz[de]isoquinoline-1,3-dione;
 (d) N-[2-(4-(5-fluoro-3-indolyl)piperidino)ethyl]-8-quinolinesulfonamide;
 (e) N-[2-(4-(6-fluoro-3-indolyl)piperidino)ethyl]-8-quinolinesulfonamide;
 (f) N-[3-(4-(6-fluoro-3-indolyl)piperidino)propyl] isoquinoline-1-carboxamide;
 (g) N-[3-(4-(6-fluoro-3-indolyl)piperidino)propyl]-6-methoxyquinoline-4-carboxamide, or physiologically acceptable salts thereof.

3. A pharmaceutical composition comprising at least one compound of the formula I according to claim 1 and/or one of its physiologically acceptable salts and a pharmaceutically acceptable excipient.

4. A method for controlling disease which comprises administering to a patient in need thereof a disease-controlling effective amount of a compound of claim 1 or physiologically acceptable salt thereof.

5. A compound according to claim 1, wherein $R^1$ is F, Cl, Br or I and $R^2$ is carboxamidonaphthyl or sulfonamidonaphthyl.

6. A compound according to claim 1, wherein $R^1$ is F, Cl, Br or I and $R^2$ is carboxamidoquinolinyl or sulfonamidoquinolinyl.

7. A compound according to claim 1, wherein $R^1$ is F, Cl, Br or I and $R^2$ is 2,3-dihydro-1H-benz[de]-isoquinoline-1,3-dione radical.

8. A compound according to claim 1, wherein $R^1$ is F, and $R^2$ is carboxamidonaphthyl or sulfonamidonaphthyl and $R^1$ is located in the 4-position of the indole radical.

9. A compound according to claim 1, wherein $R^1$ is F, $R^2$ is carboxamidoquinolinyl or sulfonamidoquinolinyl and $R^1$ is located in the 5- or 6-position of the indole radical.

10. A compound according to claim 1, wherein $R^1$ is F, $R^2$ is 2,3-dihydro-1H-benz[de]isoquinoline-1,3-dione radical and $R^1$ is located in the 5- or 6-position of the indole radical.

11. A method for treating or controlling a disease treatable or controllable by anxiolytic, antidepressant and/or antihypertensive activity which comprises administering to a patient an anxiolytic, antidepressant and/or antihypertensive effective amount of a compound of claim 1 or a physiologically acceptable salt thereof.

12. A method for treatment or control of extrapyramidal motor side effects of neuroleptics, disorders of the central nervous system, side effects from hypertension treatment, therapy of acromegaly, hypogonadism, secondary amenorrhoea, premenstrual syndrome or undesired puerperal lactation, therapy of cerebral disorders or control of sequelae of cerebral infarct which comprises administering to a patient an effective amount of a compound of claim 1 or a physiologically acceptable salt thereof.

13. The method of claim 4, wherein the compound is administered in a daily dose of 0.001 to 10 mg/kg of body weight.

14. The method of claim 11, wherein the compound is administered in a daily dose of 0.001 to 10 mg/kg of body weight.

15. The method of claim 12, wherein the compound is administered in a daily dose of 0.001 to 10 mg/kg of body weight.

16. The compound of the formula I of claim 1 wherein
 A is alkyl of 1 or 2 carbon atoms,
 $R^1$ is $CO_2H$, $CO_2CH_3$, $OCH_3$, OH, F, CN or $CONH_2$, in the 5- or 6-position,
 Q is $C_mH_{2m}$ where m is 2 or 3,
 $R^2$ is carboxamidonaphthyl, carboxamidoquinolinyl, carboxamidoisoquinolinyl, sulfonamidonaphthyl, sulfonamidoquinolinyl, sulfonamidoisoquinolinyl, 2,3-dihydro-1H-benz[de]isoquinolin-1,3-dione or 2,3-dihydro-1H-benz[de]isoquinolin-1-one, optionally substituted by OA, CN, F, Cl or Br, or a physiologically acceptable salt thereof.

17. The compound of the formula I of claim 1 wherein Q is —$CH_2$—$CH_2$—, —$CH_2$—$CH_2$—$CH_2$— or —O—$CH_2$—$CH_2$—, or a physiologically acceptable salt thereof.

* * * * *